United States Patent [19]

Mikhail et al.

[11] Patent Number: 5,099,031
[45] Date of Patent: Mar. 24, 1992

[54] PROCESS FOR THE PREPARATION OF DI- AND TRIALKYL-4'-PHTHALIMIDOMETHYL-FUROCOUMARINS

[75] Inventors: Gamal Mikhail, Odenthal; Hans-Josef Buysch, Krefeld, both of Fed. Rep. of Germany

[73] Assignee: Bayer Aktiengesellschaft, Leverkusen, Fed. Rep. of Germany

[21] Appl. No.: 608,046

[22] Filed: Oct. 31, 1990

[30] Foreign Application Priority Data

Dec. 8, 1989 [DE] Fed. Rep. of Germany ....... 3940597

[51] Int. Cl.$^5$ ........................................... C07D 405/12
[52] U.S. Cl. .................................... 548/454; 548/452
[58] Field of Search ......................................... 548/454

[56] References Cited

U.S. PATENT DOCUMENTS 3,979,393  9/1976  Kvita et al. ................... 548/454

FOREIGN PATENT DOCUMENTS 0187332  7/1986  European Pat. Off. .
0210449  2/1987  European Pat. Off. .
0235726  9/1987  European Pat. Off. .
0237833  9/1987  European Pat. Off. .

OTHER PUBLICATIONS

Isaacs et al., J. Labelled Compounds and Radio Pharmaceuticals vol. XIX, No. 3, pp. 345-356 (1981).
A. Guitto et al., Eur. J. Med. Chem., 16, pp. 489-494 Synthesis of some photosensitizing methylangelicins, as monofunctional reagents for DNA (1981).
F. Dall'Acqua et al., J. Med. Chem., 24(2), pp. 178-184 New Monofunctional Reagents for DNA as Possible Agents for the Photochemotherapy of Psoriasis: Derivatives of 4,5'-Dimethyllangelicin (1981).

Primary Examiner—David B. Springer
Attorney, Agent, or Firm—Sprung Horn Kramer & Woods

[57] ABSTRACT

Di- and trialkyl-4'-phthalimidomethyl-furocoumarins are prepared by reacting di- or trialkyl-furocoumarins in the presence of an acid and, if appropriate, of a polar solvent with a compound of the formula (I)

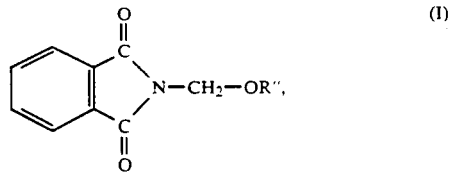

in which
R" represents hydrogen, a second phthalimidomethyl group, $C_1$- to $C_4$-alkyl or $C_1$- to $C_6$-acyl, where, when using trialkyl-furocoumarins, R" does not represent hydrogen.

10 Claims, No Drawings

PROCESS FOR THE PREPARATION OF DI- AND TRIALKYL-4'-PHTHALIMIDOMETHYL-FUROCOUMARINS

The present invention relates to a particularly advantageous process for the preparation of di- and trialkyl-4'-phthalimidomethyl-furocoumarins, in particular of 4,5'-dialkyl-4'-phthalimidomethyl-angelicins and 4,5',8-trialkyl-4'-phthalimidomethyl-psoralens.

Di- and trialkyl-4'-phthalimidomethyl-furocoumarins are important intermediates for the preparation of di- and trialkyl-4'-aminomethyl-furocoumarins which, in turn, are intermediates for the preparation of chemotherapeutics (see A. Guitto et al., Eur. J. Med. Chem. 16, 489 (1981)) and are used as building blocks for the preparation of reagents for the labelling of nucleic acids (see EP-OSs (European Published Specifications) 235,726, 237,833, 210,449 and 187,332).

It is known to prepare di- and trialkyl-4'-phthalimidomethyl-furocoumarins by first chloromethylating di- or trialkyl-furocoumarins with chloromethyl methyl ether and reacting the di- and trialkyl-4'-chloromethyl-furocoumarins thus obtained with potassium phthalimide (see F. Dall'Acqua et al., J. Med. Chem. 24 (2), pp. 178-184 (1981)). It is disadvantageous in this process that two reaction steps are required in order to get to the desired product, and that it requires the use of the easily volatile and highly carcinogenic chloromethyl methyl ether and only gives the desired product in yields of about 15% of theory.

It is further known to prepare 4,5',8-trialkyl-4'-phthalimidomethyl-psoralens by reacting 4,5',8-trialkylpsoralens with N-hydroxymethylphthalimide. The yield in this case attains 70% of theory (J. Labelled Compounds and Radiopharmaceuticals, Vol. XIX (3), 345 (1981)) and is still capable of improvement.

A process for the preparation of di- and trialkyl-4'-phthalimidomethyl-furocoumarins has now been found, which is characterized in that di- or trialkylfurocoumarins are reacted in the presence of an acid and, if appropriate, of a polar solvent with a compound of the formula (I)

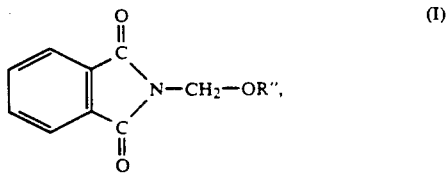

in which

R" represents hydrogen, a second phthalimidomethyl group, $C_1$- to $C_4$-alkyl or $C_1$- to $C_6$-acyl, where, when using trialkyl-furocoumarins, R" does not represent hydrogen.

The process according to the invention can be illustrated, for example, by the following reaction equations:

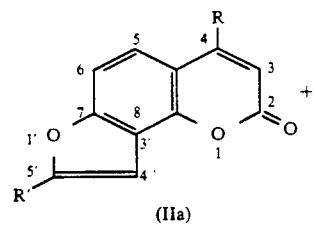

(IIa)

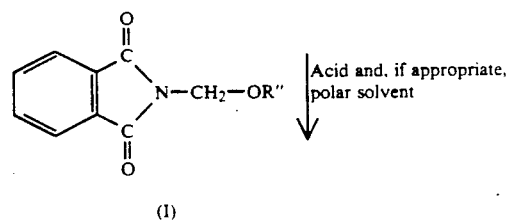

Acid and, if appropriate, polar solvent

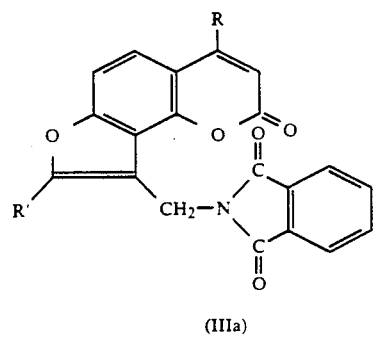

(IIIa)

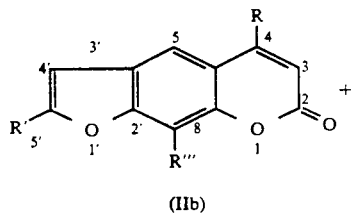

(IIb)

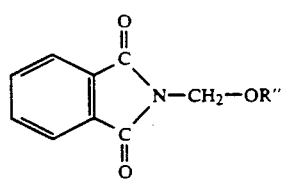

(I), but R" only corresponds here to a second phthalimidomethyl group

Acid and, if appropriate, polar solvents

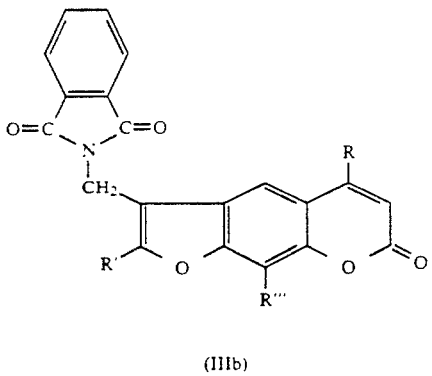

(IIIb)

In the formulae (IIa) (=4,5'-dialkylangelicins), (IIIa) (=4,5'-dialkyl-4'-phthalimidomethyl-angelicins), (IIb) (=4,5',8-trialkylpsoralens) and (IIIb) (=4,5',8-trialkyl-4'-phthalimidomethyl-psoralens), R, R' and, if present, R''' preferably independently of one another represent a $C_1$-$C_{10}$-alkyl radical. Particularly preferably, R, R' and, if present, R''' are identical. Very particularly preferably, R, R' and, if present, R''' each denote a methyl radical.

The compounds of the formula (I) are bis-N-methylphthalimido ethers (R''=a phthalimidomethyl group), N-hydroxymethylphthalimide (R''=hydrogen), alkyl N-methylphthalimido ethers (R''=$C_1$- to $C_4$-alkyl) or N-methylphthalimido esters (R''=$C_1$- to $C_6$-acyl). Of these compounds, bis-N-methylphthalimido ether is preferred.

The starting compounds of the formulae (I), (IIa) and (IIb) are known.

They can be employed, for example, in a molar ratio of (I):(IIa) or (I):(IIb) such as 1:1 to 10:1. Preferably, this ratio is 1:1 to 2:1.

The use of starting compounds of the formula (IIa) (=4,5'-dialkylangelicins) is preferred to the use of starting compounds of the formula (IIb) (=4,5',8-trialkylpsoralens).

Suitable acids, for example, are those which have a pKa value of less than 2. Acids having a pKa value of less than 1 are preferred, those having a pKa value of less than 0.1 are particularly preferred. Examples which may be mentioned are: trifluoroacetic acid, methanesulfonic acid, sulphuric acid and trifluoromethanesulfonic acid. Mixtures of trifluoroacetic acid and trifluoromethanesulfonic acid are particularly preferred. Relative to the compound of the formula (I) employed, for example, 0.1 to 10 equivalents of acid can be employed. Preferably, this amount is 0.8 to 1.2 equivalents.

Suitable solvents are protic and aprotic solvents. Suitable protic solvents are, for example, acetic acid, monofluoroacetic acid, monochloroacetic acid, monofluoromethanesulfonic acid and monochloromethanesulfonic acid. Suitable polar solvents are, for example, chloroform or acetonitrile.

The process according to the invention can be carried out, for example, at temperatures in the range $-10°$ to $+120°$ C. Temperatures in the range $15°$ to $90°$ C. are preferred.

The reaction is in general complete after a few hours, for example 2 to 48 hours.

The reaction mixture which is then present can be worked up, for example, by freeing it of volatile constituents in vacuo, mixing the residue (if desired after drying) with water, then extracting, for example with chloroform, and causing the di- or trialkyl-4'-phthalimidomethyl-furocoumarin obtained to crystallize by concentration of the extracting agent. The reaction mixture can also be worked up, for example, by column chromatographic methods.

The process according to the invention has a number of advantages. It permits the preparation of 4,5'-dialkyl-4'-phthalimidomethyl-angelicins in only one reaction step, avoiding the handling of volatile and carcinogenic substances and in substantially higher yields than in known processes. The yields in the preparation of 4,5'-dialkyl-4'-phthalimidomethyl-angelicins, according to the invention, are above 65% of theory, frequently above 90% of theory. It is particularly surprising that such high yields are attainable here using the process according to the invention, as the starting material has more than one position (see formula (IIa), positions 5, 6 and 4') in which the reagent of the formula (I) can attack. Surprisingly, in the process according to the invention a very selective attack takes place in the 4'-position In the preparation of 4,5',8-trialkyl-4'-phthalimidomethyl-psoralens, according to the invention, it is surprising that the yields can be considerably increased by the use of bis-N-methylphthalimido ether instead of N-hydroxymethylphthalimide.

The reaction of the di- and trialkyl-4'-phthalimidomethyl-furocoumarins prepared according to the invention to give the corresponding 4'-aminomethylene compounds can be carried out in a known manner, for example by reaction with hydrazine (see, for example, F. Dall'Acqua et al., loc. cit.), just like the reaction of these amino compounds to give therapeutics and reagents for the labelling of nucleic acids (see the literature references about this mentioned at the beginning).

EXAMPLE 1

4,5'-Dimethyl-4'-phthalimidomethyl-angelicin 18.83 g (56.0 mmol) of bis(phthalimidomethyl), ether were added to a solution of 10.5 g (46.7 mmol) of 4,5'-dimethylangelicin in 100 ml of trifluoroacetic acid. The solution was cooled to 0° C., and a solution of 7.33 g (49 mmol) of trifluoromethanesulfonic acid in 60 ml of trifluoroacetic acid was slowly added dropwise under nitrogen with vigorous stirring. The reaction mixture was stirred at room temperature for 48 hours. The volatile constituents were evaporated in vacuo and a reddish brown solid was thus obtained which was dried in a desiccator over KOH. The residue was suspended in 300 ml of water and extracted twice with 600 ml of chloroform each time, dried over $Na_2SO_4$, filtered through silica gel, concentrated on a rotary evaporator and crystallized from toluene/petroleum ether. 15.55 g (83% of theory) of 4,5'-dimethyl-4'-phthalimido-angelicin were obtained, m.p. 250° to 253° C.

EXAMPLE 2

4,5'-Dimethyl-4'-phthalimidomethyl-angelicin 3.9 g (22 mmol) of N-hydroxymethylphthalimide were added to a solution of 4.28 g (20 mmol) of 4,5'-dimethylangelicin in 40 ml of trifluoroacetic acid. The solution was cooled to 0° C., and a solution of 3.29 g (22 mmol) of trifluoromethanesulfonic acid in 20 ml of trifluoroacetic acid was slowly added dropwise under nitrogen with vigorous stirring. The reaction mixture was stirred at room temperature for 48 hours. Working up was carried out as described in Example 1. 3.1 g (42% of theory) of 4,5'-dimethyl-4'-phthalimido-angelicin were obtained.

EXAMPLE 3

4,5',8-Trimethyl-4'-phthalimidomethyl-psoralen 0.925 g (2.89 mmol) of bis-(phthalimidomethyl) ether were added to a solution of 1.015 g (4.45 mmol) of trioxsalen in 5 ml of trifluoroacetic acid. The solution was cooled to 0° C., and a solution of 0.67 g (4.45 mmol) of trifluoromethanesulfonic acid in 2 ml of trifluoroacetic acid was slowly added dropwise with vigorous stirring under nitrogen. The reaction mixture was stirred at room temperature for 48 hours and then worked up as described in Example 1. 1.51 g (91% of theory) of 4,5',8-trimethyl-4'-phthalimidomethyl-psoralen were obtained, m.p. 268° to 270° C.

What is claimed is:

1. A process for the preparation of di- and trialkyl-4'-phthalimidomethyl-furocoumarins, in which a di- or trialkyl-furocoumarine is reacted in the presence of an acid with a compound of the formula

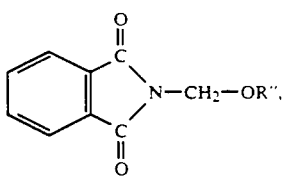

in which

R" represents hydrogen, a second phthalimidomethyl group, $C_1$- to $C_4$-alkyl or $C_1$- to $C_6$-acyl, where, when using trialkyl-furocoumarins, R" does not represent hydrogen.

2. The process of claim 1, in which as oialkyl-furocoumarine a 4,5'-dialkylangelicin of the formula (IIa)

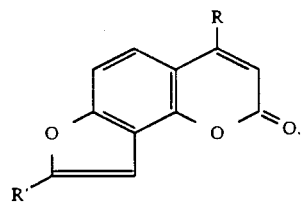

is employed
in which
R and R' independently of one another represent a $C_1$-$C_{10}$-alkyl radical.

3. The process of claim 1, in which as trialkyl-furocoumarine a 4,5'-8-trialkylpsoralen of the formula (IIb)

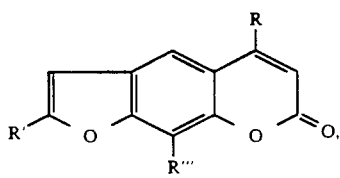

is employed
in which
R, R' and R''' independently of one another represent a $C_1$-$C_{10}$-alkyl radical.

4. The process of claim 2, in which R and R' each represent a methyl radical.

5. The process of claim 3, in which R, R' and R''' each represent a methyl radical.

6. The process of claim 1, in which bis-N-methylphthalimido ether is employed as the compound of the formula (I).

7. The process of claim 1, which is carried out at temperatures in the range $-10°$ to $+120°$ C.

8. The process of claim 1, in which the di- or trialkyl-4'-phthalimidomethyl-furocoumarine obtained is purified by extraction and subsequent concentration of the extracting agent.

9. The process of claim 8, in which chloroform is used as the extracting agent.

10. The process of claim 1, which is carried out in the presence of a polar solvent.

* * * * *

UNITED STATES PATENT AND TRADEMARK OFFICE
CERTIFICATE OF CORRECTION

PATENT NO. : 5,099,031

DATED : March 24, 1992

INVENTOR(S) : Mikhail et al.

It is certified that error appears in the above-identified patent and that said Letters Patent is hereby corrected as shown below:

Col. 5, lines 45-46    Delete " oialkylfurocoumarine " and substitute -- dialkylfurocoumarine --

Signed and Sealed this

Second Day of November, 1993

Attest:

BRUCE LEHMAN

Attesting Officer

Commissioner of Patents and Trademarks